United States Patent [19]

Levin

[11] Patent Number: 4,834,946

[45] Date of Patent: May 30, 1989

[54] APPARATUS FOR BLOT SCREENING NUMEROUS, SMALL VOLUME, ANTIBODY SOLUTIONS

[76] Inventor: Andrew E. Levin, 145 Bishop Allen Drive, Cambridge, Mass. 02139

[21] Appl. No.: 11,291

[22] Filed: Feb. 5, 1987

[51] Int. Cl.$^4$ .................. C12M 1/12; C12M 1/20; G01N 33/48

[52] U.S. Cl. .................. 422/101; 435/293; 435/301

[58] Field of Search ............ 422/100, 101; 435/285, 435/288, 292, 293, 301

[56] References Cited

U.S. PATENT DOCUMENTS

| | | | |
|---|---|---|---|
| 4,493,815 | 1/1985 | Fernwood | 422/101 |
| 4,526,690 | 7/1985 | Kiovsky et al. | 422/101 X |
| 4,591,567 | 5/1986 | Britten et al. | 435/292 X |
| 4,681,853 | 7/1987 | Hardy et al. | 435/285 |
| 4,713,349 | 12/1987 | Levin | 436/515 |

OTHER PUBLICATIONS

Turbo Blot TM brochure by American Bio Nuclear.
Flyer, "Immunetics", (approximately June/July, 1986), 1 page-front and back.

*Primary Examiner*—Barry S. Richman
*Assistant Examiner*—Jill Johnston
*Attorney, Agent, or Firm*—Harness, Dickey & Pierce

[57] ABSTRACT

A cover plate, having a lower, flat surface containing an array of numerous, parallel, closely spaced apart, downwardly opening channels, is releasably clamped upon a flat support plate surface. The channels each have inlet and outlet holes communicating with the upper surface of the cover plate. A paper-like, resilient cushion sheet is clamped between the plate surfaces and a paper-like membrane, carrying a pattern of antigen-like material, is arranged between the sheet and the cover plate channeled surface. The channels are very narrow, shallow and many times longer than their widths and are closed by the stripe-like portions of the membrane which overlie the channels. The cushion sheet is compressed between adjacent channels and bulges upwardly at each of the channels to thereby bulge the membrane stripe-like portions into dome-shaped cross-sections extending into the channels. This reduces the volumes of the channels and increases the surface areas of the membrane stripe-like portions that are exposed within the channels. Numerous drop-size samples of antibody-type solutions are inserted into the channels through channel inlet holes, that extend through the cover plate, for reacting with the material carried on the stripe-like portions of the membrane. A removable manifold having a pair of elongated grooves may be temporarily applied upon the cover plate so that the grooves overlie all of the channel inlet holes and all of the channel outlet holes for rapidly, simultaneously filling and draining all the channels.

19 Claims, 3 Drawing Sheets

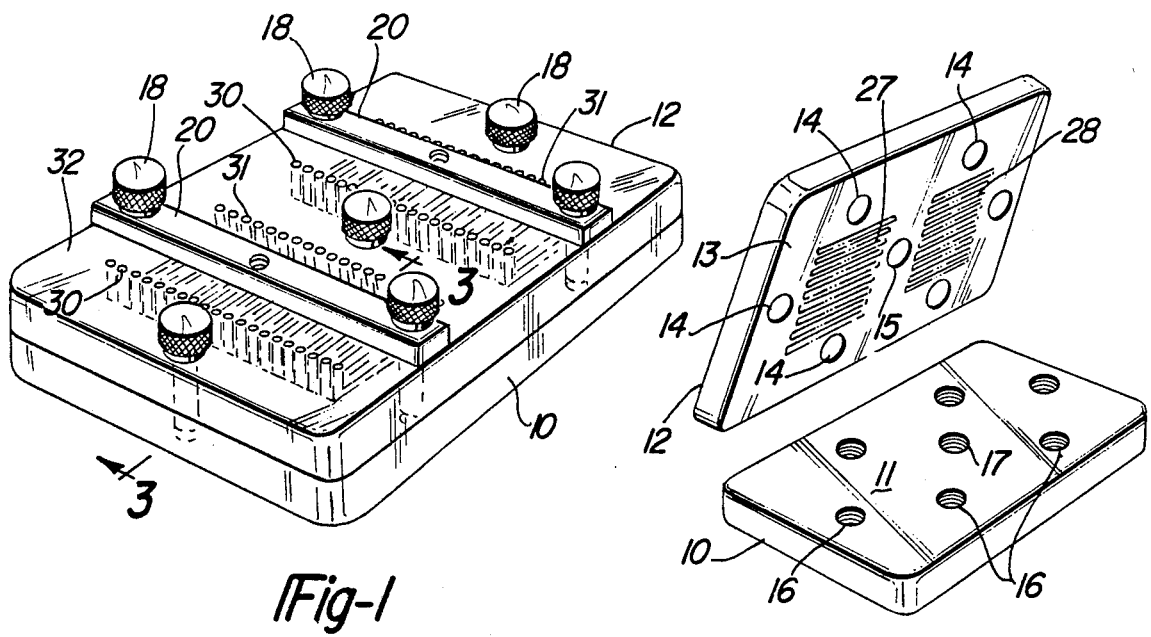
*Fig-1*
*Fig-2*
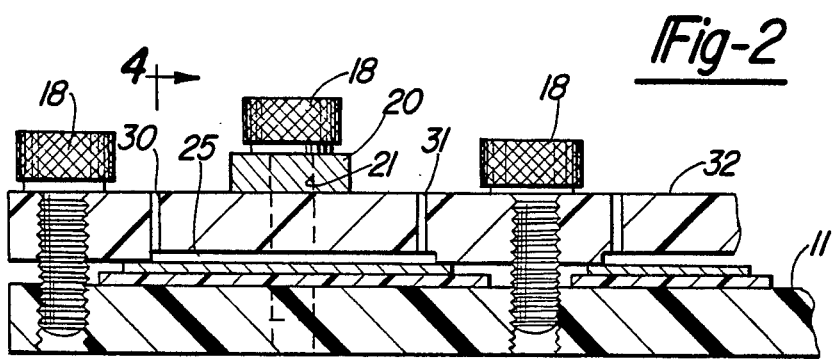
*Fig-3*
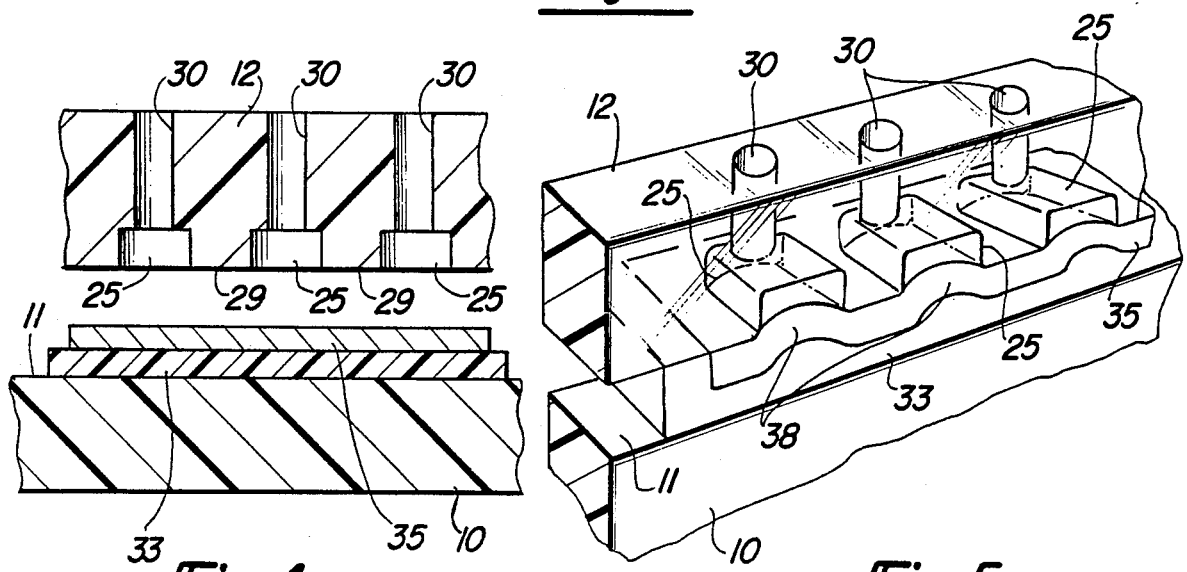
*Fig-4*
*Fig-5*

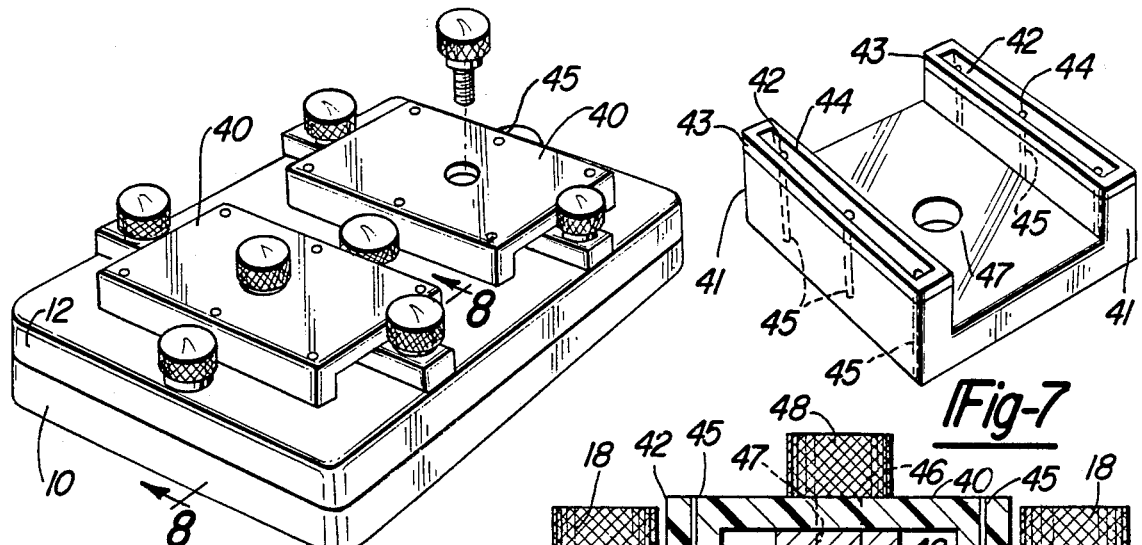
Fig-6
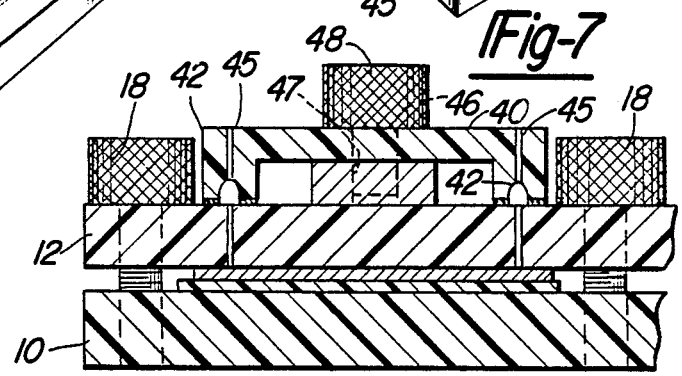
Fig-7
Fig-8
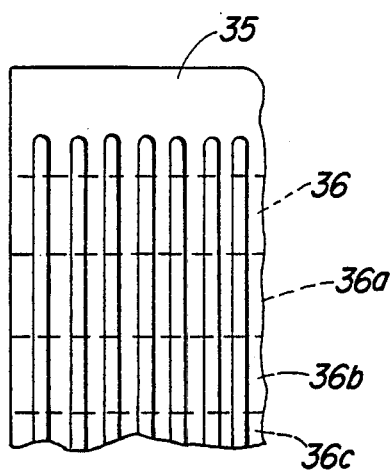
Fig-9
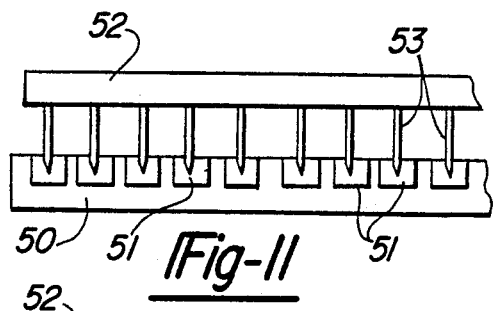
Fig-11
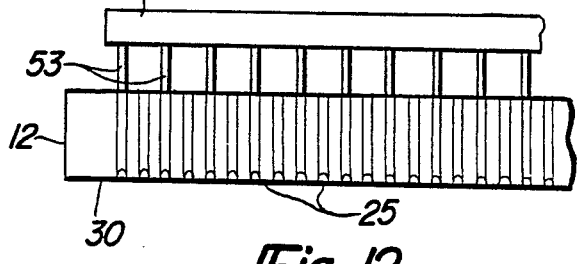
Fig-12
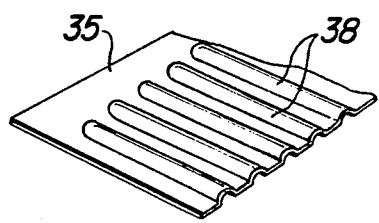
Fig-10

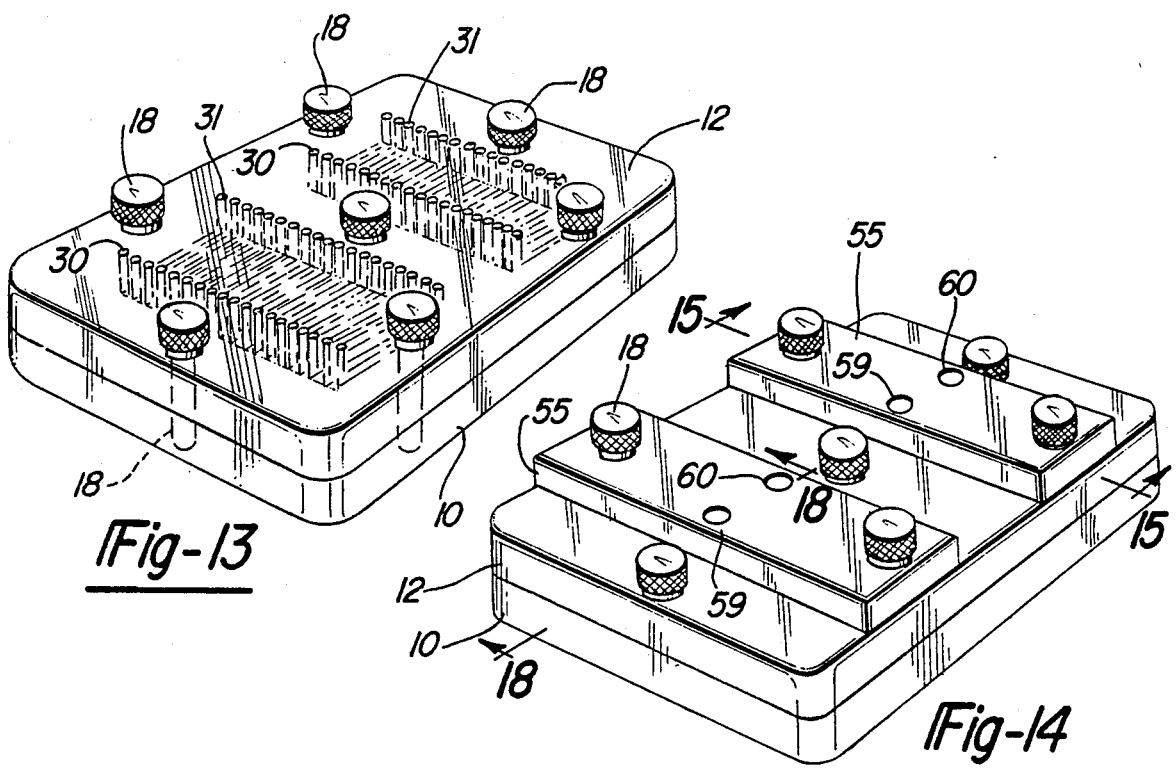
Fig-13
Fig-14
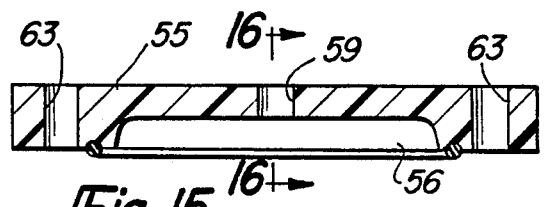
Fig-15
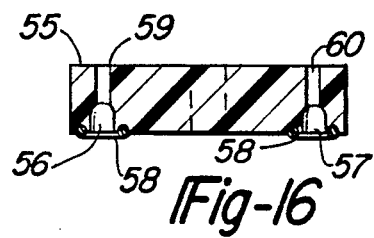
Fig-16
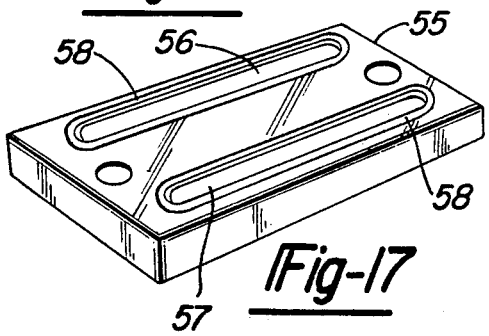
Fig-17
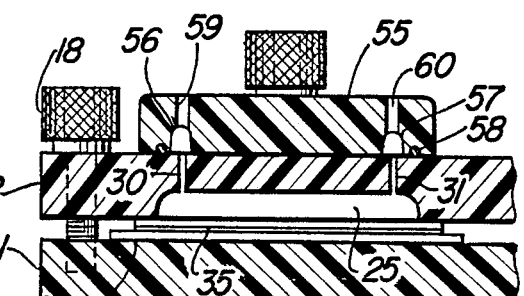
Fig-18
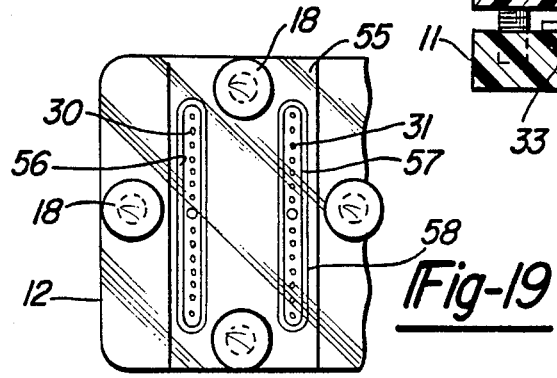
Fig-19

APPARATUS FOR BLOT SCREENING NUMEROUS, SMALL VOLUME, ANTIBODY SOLUTIONS

BACKGROUND

The apparatus of this invention is used in screening samples of antibody solutions on nitrocellulose or other transfer membranes on which proteins or antigens have been immobilized. The membranes, commonly made of nitrocellulose paper-like sheets, carry proteins which have been electroblotted from polyacrylamide gels. The gel may include one sample that is electrophoresed across the entire gel and may be used for the screening of a number of antibodies against the same antigen pattern. Alternatively, antibodies may also be screened against different antigens electrophoresed in separate vertical lanes on the same gel.

A number of the same or different antibody solutions may be applied against a single transfer membrane and through suitable processing, observable results of the reactions can be used for a screening analysis.

In this type of screening, it is desirable to apply a relatively large number of separate rows or stripes of the sample solutions under assay upon a single transfer membrane for side-by-side reading of the test results. Also, it is normal for many test purposes to utilize transfer membranes having a relatively large number of different bands of immobilized anitgens located along the length of the membrane. In those instances, the stripes of antibody solutions are applied transversely to the numerous bands. Thus, observable test results occur at various locations along the lengths of the stripes where they intersect with the different bands. This provides side-by-side comparisons of antibody blotting profiles.

An apparatus for conducting such screening tests has been developed in which the transfer membrane, upon which the antigens have been immobilized, is positioned between a pair of plates that are fastened together. The uppermost plate has an array of parallel grooves or channels that open downwardly against the membrane. The channels may be filled with one or more different antibody samples so that parallel stripes of such samples are incubated on the membrane for the desired side-by-side comparisons.

The apparatus of this invention relates to improvements to the foregoing apparatus, particularly in reducing the amount of antibody sample solutions required for conducting the screening and in providing a maximum screening capacity notwithstanding the reduction in the volume of antibody solution. Generally, this apparatus, which is a laboratory tool, assists in more efficiently conducting the screening operation by reducing the amount of antibody solution needed, while at the same time producing wider, more easily readable, antibody stripes upon a single membrane. In addition, the apparatus may include means for substantially reducing the time necessary for performing the screening operation.

SUMMARY OF INVENTION

In a presently known apparatus for screening samples of antibody solutions against transfer mediums carrying immobilized antigens, the heavy paper-like nitrocellulose transfer membrane is placed upon a flat surface of a base plate and covered with a plate having numerous, long grooves or channels formed in its lower surface and which open against the membrane. The plates are tightly clamped together, as by using large screws, so that the grooves are sealed, one from another, by the membrane portions that are located between adjacent channels. Inlet and exit holes, formed through the upper plate, extend into the respective channels for the application and removal of the test solutions into and from the channels. The apparatus may be placed upon a rocker table, where desired, or held statically for a period of time to permit incubation. Thereafter, the antibody solutions are removed from the channels, such as by vacuum aspiration or recovery by a pipette, and the transfer membrane is removed by unclamping the plates. Thereafter, other standard laboratory procedures may be followed for ultimately obtaining test results in the form of observable marks upon the membrane.

The invention herein contemplates means for substantially reducing the amount of antibody solution needed for the conduct of the screening test in the foregoing apparatus, and also, providing a means for rapidly rinsing the nitrocellulose membrane while it is in place in the apparatus and, consequently, removing excess solution remaining from the previous step of the assay. The reduction in the amount of solution needed for the test is accomplished by utilizing a relatively low density, resilient or spongy, paper-like cushion sheet between the membrane and the surface of the base plate. The sheet is tightly compressed, by the pressure of the clamped plates, in the areas between the parallel grooves or channels, but bulges resiliently towards the openings of the channels. This resilient or spongy bulging causes the stripe-like portions of the membrane which overlie the openings of the long, narrow and shallow channels, to bulge inwardly of the channels in dome-like cross-sectional shapes. That reduces the volume of the space within each channel and, therefore, considerably reduces the amount of test solution needed to fill the channel for screening purposes. Despite the reduction in volume, the rounded or dome-like in cross-section embossments formed by the stripes of membrane material extending into the channels, substantially increase the amount of membrane surface area which is exposed to the solution contained within the channels. That is, the membrane portion which is forced into each channel simultaneously reduces the volume of solution needed to fill the channel and increases the amount of membrane surface area that is exposed to the solution. Moreover, because the embossments stand out, visual identification and scanning the results are more convenient.

In addition, the parallel channels are spaced apart distances which correspond to the conventional spacing found in standard plates, such as "Microtiter" (a trademark of Dynatech, Inc.) plates. Such plates are formed with large numbers of wells which contain samples to be tested, e.g. 96 wells in an 8×12 well inch array in a 'Microtiter' plate. These wells are spaced apart predetermined distances, one from another, for utilization of these plates in standard, laboratory test equipment. The spacings between the wells are considerably greater than the spacing between adjacent channels in the apparatus of this invention. However, by using standard multiple pipetters, such as an eight-channel pipetter, the pipetter tips may be filled from adjacent wells and then emptied into alternate channels. This can be repeated until all the channels are filled. For example, the spacing between the adjacent channels in the cover plate may be such that the pipetter fills every third channel at one time. Thus, the number of filling operations is reduced. To fill 24 channels, only three operations would be necessary by filling every third channel in each operation with a standard, commercially available, eight-channel pipetter.

For purposes of filling the channels, each channel is provided with an inlet and outlet opening which extends upwardly from the channel to the upper surface of the cover plate. The tips of standard pipetters fit into these openings.

The means for rapidly rinsing the membrane comprises a unique manifold which permits filling and emptying all the channels simultaneously. This enables continuous rinsing of the membrane while it is positioned in the apparatus. This is useful, for example, in removing excess solution remaining from the prevous step of an assay.

The manifold is arranged transversely of, and extends over, all the adjacent parallel channels. The bottom surface of the manifold has grooves that overlap the aligned rows of inlet and outlet holes of the channels. The grooves have openings that extend to the upper surface of the manifold. Thus, a rinsing solution may be flowed into an opening in the surface of the manifold for travel through one of the manifold grooves into the row of inlet holes to fill the channels. Likewise, the solution may be removed through the manifold groove covering the outlet holes. The solution may be forced through the system under positive pressure from a pump arranged in an inlet line to the manifold or may be drawn through the system by a vacuum source located in an outlet line from the manifold. This arrangement permits continuously circulating fluid through the channels for rapidly flushing all of the channels in the course of the screening procedure. For example, the time needed to perform a washing step can be reduced from a number of minutes to a number of seconds.

One object of this invention is to provide an apparatus which makes it possible to obtain side-by-side comparisons of antibody blotting profiles simply, quickly and definitively along parallel strips which are easy to observe and analyze. Significantly, the equipment permits the use of a minimal volume of antibody solution while giving a maximum stripe width and permits the simultaneous conduct of a relatively large number of screenings on a single membrane.

Another object of this invention is to provide a flexible apparatus wherein the number of samples tested on a single membrane at one time may be varied up to a maximum. Because of a removable and replaceable manifold, the entire apparatus may be suitably flushed in the course of a test procedure with minimal time and effort regardless as to whether all or only some of the channels are utilized in a specific test.

Yet a further object of this invention is to provide a spongy or resilient cushion which deforms portions of the transfer membrane into the channels to produce wider test stripes to reduce the channel volume and to better seal against leakage between channels. Also, the deformed embossments make assay results easier to read by clearly identifying one lane from another on the membrane. The cushion may be repeatedly reused and may be easily cleaned for such reuse.

These and other objects and advantages of this invention will become apparent upon reading the following description, of which the attached drawings form a part.

DESCRIPTION OF DRAWINGS

FIG. 1 shows a perspective view of the assembled apparatus.

FIG. 2 illustrates a perspective view of the upper, cover plate and the lower, base plate, separated from each other.

FIG. 3 is an enlarged, cross-sectional, elevational view taken in direction of arrows 3—3 of FIG. 1.

FIG. 4 is an enlarged, fragmentary, cross-sectional view taken as if in the direction of arrows 4—4 of FIG. 3 and schematically showing the cover plate raised a short distance above the base plate.

FIG. 5 is a perspective, fragmentary, schematic (e.g., cross-sectional cross-hatch lines omitted for clarity of interior lines), enlarged view of the cover plate compressed against the base plate for deforming the transfer membrane into adjacent channels.

FIG. 6 is a schematic view showing the apparatus with manifold blocks attached for filling or emptying the channel simultaneously.

FIG. 7 is an enlarged, perspective view of a manifold in inverted position to show the grooves in the manifold legs.

FIG. 8 is an enlarged, cross-sectional view taken in the direction of arrows 8—8 of FIG. 6, illustrating a manifold positioned on the apparatus.

FIG. 9 is an enlarged, plan view of a fragment of the transfer medium or membrane after compression within the apparatus.

FIG. 10 is a fragmentary, perspective view of a corner of the transfer membrane showing the impressed stripes resulting from deformation into the channels.

FIG. 11 is a schematic view illustrating the filling of gang-pipetter from a "Microtiter" plate containing separate wells.

FIG. 12 is a schematic view showing the gang-pipetter used to simultaneously fill alternate channels in the apparatus.

FIG. 13 is a perspective view of the apparatus assembled without the crossbars.

FIG. 14 is a perspective view of the apparatus with modified manifolds in place.

FIG. 15 is a cross-sectional view of the modified manifold, per se, taken in the direction of arrows 15—15 on FIG. 14.

FIG. 16 is a cross-sectional view of the manifold taken in the direction of arrows 16—16 of FIG. 15.

FIG. 17 is a perspective view of the lower surface of the manifold of FIG. 15.

FIG. 18 is an enlarged, cross-sectional, fragmentary view taken in the direction of arrows 18—18 of FIG. 14.

FIG. 19 is a schematic, fragmentary plan view showing the grooves of the manifold of FIG. 14 overlying the rows of openings in the upper plate.

DETAILED DESCRIPTION

Referring to FIGS. 1–3, the apparatus includes a base plate 10 having a flat, upper support surface 11. An upper, cover plate 12 is arranged above the base plate. The cover plate has a lower, flat cover surface 13.

The two plates are releasably clamped together by a manually releasable clamping means. The drawings illustrate a number of screw-receiving holes 14 around the edges of the cover plate 12. In addition, a central screw hole 15 is formed at the central part of the plate. These screw holes register with base plate threaded holes 16 around the edges of the base plate and a central, threaded screw hole 17 in the base plate. Large screws 18 extend through the registered screw holes and threadedly engage with the threads formed in the base plate holes.

Preferably, the plates are made of a transparent plastic material, such as "Plexiglass". The particular kind of plastic used for the plates may be any commercially available material which is sufficiently inert and rigid for the purpose. By using a transparent plastic, the user of the apparatus is able to observe the filling and the contents of the channels.

The screws may be made of a plastic material which is relatively strong and inert. By providing the screws with enlarged heads, which may be knurled or provided with surface grooving, the screws can be easily loosened and tightened manually by the user. However, other suitable forms of fasteners may be used.

Metal crossbars 20 may be positioned upon the upper, cover plate 12 for further rigidifying the plates and ensuring that the plates are uniformly contacted together during the compression caused by the screws. The crossbars may also function to support and enable the use of manifold blocks which will be described below. In some instances, the crossbars may be omitted (e.g., see FIG. 13). These crossbars are provided with screw-receiving end holes 21 (see FIG. 3) through which some of the screws 18 are inserted so that the crossbars are held in place by some of the same screws which otherwise fasten the plates together.

While the metal bars may be formed of any suitable, commercially available material, thick aluminum bars have been found to be suitable for this purpose. The specific aluminum material and the size of the bar may be varied considerably.

A large number of grooves or channels 25 are formed in the lower, cover surface 13 of the upper, cover plate 12. These grooves are arranged in two, separated arrays 27 and 28 as illustrated in FIG. 2. The grooves are shallow, very narrow, and of lengths which are many times their widths. For example, each of the grooves may have a depth of 0.040 inches, plus or minus 0.005 inches, a width of approximately 1.5 to 5 millimeters and length which is more than 20 times the width, such as 5.5 centimeters. The spacing between adjacent pairs of grooves may be roughly equal to or slightly more or less than the width of an individual groove. The precise widths, depths and lengths of the grooves may be varied for particular purposes.

The grooves are schematically illustrated in FIG. 4 wherein three adjacent grooves 25 are separated by lands 29 which are areas of the lower cover surface 13 of the upper cover plate 12. The grooves are provided with inlet holes 30 (see FIGS. 3 and 4) and outlet holes 31 (see FIG. 3) through which the individual channels or grooves may be filled or drained. The holes are preferably aligned in rows which open at the upper surface 32 of the cover plate 12, as illustrated in FIG. 1.

A spongy or very resilient, cushion support sheet 33 is placed upon the upper surface of the base plate for overlying each of the two arrays of grooves. That is, a separate sheet may be provided for each array. The cushion sheet is relatively thin, such as on the order of about 0.015-0.040 inches in thickness so that it is similar to a thick paper. Preferably, it is formed of a foam plastic material, such as a polyethylene, closed cell foam. A suitable example of such material is "Plastazote P-4053", sold by BXL Plastics Ltd., of Surrey, England. This is a spongy material which can be compressed and which will tend to bulge between lines of compression. Any similar spongy or resilient material having the same characteristics can be used. Preferably, such material has a low density to provide the compression and bulging effect desired. For example, the material mentioned above has a density of roughly in the area of 2.8 pounds per cubic foot. With the use of such resilient, dense material and with sufficiently rigid plates, a tight seal may be obtained between the plates to permit elimination of the metal cross bars.

A transfer membrane 35 of sufficient size to overlay the array of channels, or at least to overlie the channels to be used in any particular experiment, is placed upon the surface of the cushion sheet. Such membranes are typically made of a nitrocellulose, non-woven, paper-like material upon which proteins or other antigens have been immobilized. The membrane is prepared through known procedures and, therefore, the preparation of the membrane for the purpose of the apparatus described here is omitted. However, typically the membrane includes either the same or different antigens applied and immobilized afer prior separation by gel electrophoresis. Alternately, antigens may be applied to, and immobilized on, the membrane in separate horizontal strips without prior electrophoretic separation. FIG. 9 schematically illustrates a membrane 35 having different antigens applied in bands 36, 36a, 36b, 36c which extend across the membrane. The illustration of the bands 36, 36a, 36b, 36c is an over-simplification, but serves to show that the nature of the antigens may be changed along one direction of the paper-like membrane for various antibody screening purposes.

In operation, the user of the apparatus positions cushion sheets 33 upon the flat, upper surfaces of the base plates in the regions of the arrays of channels. Then he applies treated membranes 35 upon the cushion sheets, as illustrated in FIG. 4. Next, the screws 18 are inserted through the screw holes in the plates and hand tightened so as to compress the plates together. That results in the compression of the portions of the cushion sheet by the lands 29 located between the adjacent pairs of grooves 25. The stripe-like portions of the cushion sheet which overlie the grooves, however, tend to bulge upwardly towards the openings of the grooves. This results in bulging portions of the membrane into the open mouths of the grooves. Thus, the membrane, as illustrated schematically in FIG. 5, is deformed into numerous stripes 38, each of a dome-like cross-section, bulging into and closing the grooves or channels which they overlay. Consequently, the strips not only close the channels, but also reduce the volumes of the channels by extending into them. Significantly, although the volumes of the channels are each reduced by the inwardly extending stripes of the membrane, the membrane surface within each channel is increased so that a greater amount of membrane surface is exposed to the samples in the channels.

By reducing the volumes of the channels and simultaneously increasing the membrane surface area exposed to the liquids within the channels, a considerably smaller volume of sample material is needed for the screening with this apparatus. For example, an array of 28 channels, with each channel about 1.5 millimeter in width, 5.5 centimeters in length, and roughly 0.040 inches in depth, requires only about 60 microliters per channel. Without the bulging effect, each channel would need about 80 microliters, so that there is about a 20% reduction in the volume of test solution needed.

Increasing the size of the channels, as for example, to 13 centimeters in length and 2 millimeters in width, with approximately the same depth, requires only about 110 microliters per channel. An additional 25 microliters of solution would be required without the bulging.

After the solution under assay is applied to the channels, sufficient time for incubation is allowed. During that time, the apparatus may be rocked upon a conventional rocking table. After the required time has elapsed, the user releases the screw fasteners, separates the plates, and removes the membranes. At that point, the embossed stripes 38 appear, as illustrated in FIGS. 9 and 10.

Later processing of the membranes may be required, following standard testing procedures. After completely processing the membranes, observable markings will appear upon the membrane stripes, such as along the intersections with various bands of immobilized antigens upon the membrane.

Where a single sample solution is introduced in all of the channels of one array of channels, the filling of the channels and the later flushing of the solution may be more rapidly accomplished using manifold 40 illustrated in FIGS. 6–8. The manifold, which is U-shaped in cross-section, has legs 41 which overlie each of the rows of inlet and outlet holes 30 and 31 upon the upper surface 32 of the cover plate 12. The lower surface of each leg 41 is provided with an elongated groove 42 (see FIGS. 7 and 8). A resilient, sealing gasket 43, having a slot 44 aligned with the grooves, is positioned upon the lower surface of each leg. A number of holes 45 extend from each of the grooves to the upper surface of the manifold.

The manifold is secured upon the apparatus by a manually releasable fastener, such as a screw. This is accomplished by providing a screw hole 46 in the base portion of the manifold, i.e. in the portion extending between the legs 41. An aligned threaded hole 47 formed in the metal bar 20, receives a suitable screw 48 for securing the manifold upon the bar and simultaneously compressing the manifold gaskets against the upper surface of the cover plate.

With the manifold in place, liquid sample material can be flowed into one of the holes in the manifold so that the material flows through the corresponding groove and then into all of the channel holes simultaneously until the channels are filled. Later, for flushing the solution, e.g. after the incubation, fluid may be flowed into one of the manifold grooves and out of the other manifold groove for a continuous flushing. The use of the manifold permits rapid, more uniform, filling and flushing. The manifold allows a very large volume of liquid, relative to the surface area of the membrane, to be forced over the membrane. However, the volume of liquid actually in contact with the membrane at any specific time is small (e.g. only enough to fill each groove), but as the liquid is rapidly moving through the grooves and over the membrane, rinsing is more effective.

Where the channels are to be separately filled, without the manifold, it is possible to fill the channels more rapidly due to the spacing between the channel holes. That is, as illustrated in FIGS. 11 and 12, the spacing between the channels and their inlet holes is selected to correspond to the standard spacing found on conventional laboratory equipment such as a multi-well culture plate or microculture plate 50 (illustrated schematically in FIG. 11). The culture plate is formed with a number of wells 51, each containing material to be used in the screening procedure. An example of such a culture plate is one having 96 wells. The wells are spaced apart predetermined distances in order to permit the use of the plate in other laboratory equipment. Here, a standard eight tip gang pipetter 52 may be used to obtain samples from a row of wells, as shown in FIG. 11. Then, the pipetter 52 is arranged over the inlet holes in the cover plate 12 (see Fig. 12). The tips 53 are aligned with alternating inlet holes. For example, in the spacing shown in FIG. 12, each tip is arranged over and fills each third hole leading into each third channel. Then, the pipetter may be moved to fill the next alternate holes and channels.

After the screening procedure is performed in the apparatus, the parts may be separated and easily and rapidly cleaned. As can be seen, the smooth surfaces of the various parts are easily cleanable. Therefore, the apparatus can be rapidly made ready for reuse after each screening operation. All of its parts, including the cushion sheet, are reusable.

In the embodiment illustrated, the channels are formed into two arrays. However, for certain types of screening, it may not be necessary to use two separate arrays and, therefore, the device may be built with a single array of channels or even with more than the two illustrated.

FIGS. 14–19 illustrate a modified manifold block. As illustrated, the block may be formed of a rectangular in cross-section strip of a length to transversely overlie the upper surface of the cover plate. The block 55 is preferably formed of a transparent or substantially transparent plastic material, such as "Plexiglass" or the like, so that the user of the apparatus may look through it.

As shown in FIG. 14, a pair of blocks are used, each overlying one of the two groove or channel areas of the cover plate. Each block 55 has a pair of grooves 56 and 57 formed in its lower surface. Each groove is surrounded by a sealing rubber-like gasket or ring 58 which seals the groove against the upper surface of the cover plate. Each groove has an opening communicating to the opposite surface of the block. Thus, an opening 59 communicates with the groove 56, and an opening 60 communicates with the groove 57 (see FIG. 16). In addition, each block has a screw-receiving opening 63 formed at its opposite ends.

In operation, when the manifold is to be used, such as for rapidly flushing the complete set of channels in the cover plate, screws 18 at the opposite sides of the plates are manually removed. Then, the block is positioned transversely upon the cover plate and the screws are inserted through the openings 63 in the opposite ends of the block for fastening the block to the cover and base plate. Tightening the screws causes the gaskets 58 to seal against the upper surface of the cover plate.

As shown in FIG. 19, which is a view as if looking downwardly through a transparent manifold block, each groove in the manifold block overlies a row of holes which communicate through the cover plate to the channels 25 in the cover plate. Thus, liquid may be forced, such as by pressurized pumping or conversely by using a withdrawing vacuum, through inlet hole 59 in the block and into the groove 56 so that the fluid simultaneously enters the cover plate channels 25 through the openings 30. The fluid may then flow through the channels 25 and out the openings 31 in the cover plate, entering the groove 57 in the manifold block and then passing out of the block through the exit hole 60. Where desired, another inlet or exit hole may be provided in the block for handling larger volumes of liquid.

Since the block is preferably transparent, the user of the apparatus is able to observe the movement of the liquid through the block and channels to the extent desired where the material being tested is dangerous in some way, such as comprising human serum samples from patients having an infectious disease. The exit opening 60 may be connected, through a suitable tube (not shown) to a sealed receptacle for suitable disposable. Thus, the device, with the manifold, lends itself to handling and testing materials which may require special handling because they are dangerous.

Having fully described an operative embodiment of this invention, I now claim:

1. An apparatus for use in blot screening antibody-type material by simultaneously reacting a substantial number of very small volume liquid samples of such material arranged in a stripe-like pattern with a transversely arranged antigen pattern carried upon a paper-like membrane, comprising:

a base plate having an upper, flat support surface, and a cover plate having a lower, flat cover surface overlapping the base plate support surface;

manually releasable fasteners clamping the plate overlapping surfaces together;

a thin, resilient cushion support sheet positioned between and substantially covering the plate surfaces in face-to-face contact with the base plate support surface;

an array of a substantial number of parallel, closely spaced, elongated, shallow and very narrow, downwardly opening channels formed in the cover plate support surface separated by stripe-like portions;

each channel having at least one small filling hole extending through the cover plate for conveying a sample of a liquid material into the channel;

a membrane removably positioned upon said cushion sheet and arranged in face-to-face contact with the cover plate surface so that the membrane closes the channel openings, said membrane being adapted for screening samples of liquid materials;

and said resilient support sheet being resiliently compressed against the base plate support surface between the channels by the stripe-like portions of the cover plate surface that are located between the adjacent pair of channels and the cushion support sheet resiliently bulging upwardly at the channel openings and thereby bulging the stripe-like portions of the membrane into the channels for forming inwardly extending, dome-like in cross-section, bottom walls for the channels which walls simultaneously reduce the interior volumes of the channels and increase the membrane surface area exposed to liquids contained within the channels;

wherein a sample of a liquid material may be introduced within at least one of the channels and another sample of a different liquid material may be introduced within at least one of the other channels, with the portions of the membrane surface area being bulged by the resilient support sheet into the channels to close the bottom of each respective channel, reduce the volume of each respective channel by extending into each respective channel and substantially prevent leakage of sample between adjacent channels.

2. An apparatus as defined in claim 1, and further including each channel having a second, small hole extending through the cover plate communicating therewith, with the filling hole of the channels being aligned in a row near one end of the channels and the second holes being aligned in a row near the other end of the channels wherein liquid may be flowed into the channels through one row of filling holes and flowed out of the channels through another row of second holes.

3. An apparatus as defined in claim 1, wherein the width of said channels is in the range of 1.5–5 millimeters and the length of said channels is greater than 20 times such width, so that the channels may be filled with microliter, drop-size samples;

and with the distance between pairs of adjacent, parallel channels being approximately equal to the width of said channels.

4. An apparatus as defined in claim 3, wherein the resilient cushion support sheet is formed of a foam type of plastic material which is characterized by being relatively inert to the specimen materials.

5. An apparatus as defined in claim 1, and further including a manifold block releasably secured upon the cover plate and having a downwardly opening groove which extends over the filling holes, and an opening extending through the block communicating the groove with the upper end of the block, so that a liquid may be flowed through the opening, the groove and the cover plate filling holes and into a number of channels simultaneously.

6. An apparatus as defined in claim 1, and including a second array of parallel channels, similar to the first-mentioned array of channels, located in the lower, flat cover surface of the cover plate adjacent to the first-mentioned array of channels and having similar filling holes extending through the cover-plate, wherein a second cushion support sheet, similar to the firstmentioned sheet, is arranged between the base plate, and cover plate and an additional membrane, is located between the resilient sheet and the base plate, at which the second array is formed, whereby two separate arrays may be simultaneously used for screening.

7. An apparatus as defined in claim 1, wherein said membrane includes a nitrocellulose material.

8. An apparatus as defined in claim 7, wherein said resilient support sheet includes a polyethylene material.

9. An apparatus as defined in claim 1, and wherein said filling holes are aligned in a row near one end of the channels, and further comprising a row of second holes communicating each channel to the upper surface of the cover plate and the second holes being aligned in a row;

a manifold block releasably secured upon the cover plate and having a pair of spaced apart, downwardly opening grooves, with one of said grooves communicating with said row of filling holes and the other of said grooves communicating with said row of second holes;

each groove having an opening extending through the manifold block and communicating the respective groove to the upper end of the block;

whereby liquid may be flowed through one opening and its respective groove and said filling holes into all of the channels and the row of second holes permit the liquid to flow out of the channels so that liquid may be circulated into and out of all of the channels simultaneously.

10. An apparatus as defined in claim 9, wherein said manifold block is generally U-shaped in cross-section, formed with an integral base and legs, and being of a length and width sufficient to overlap all of the parallel channels in the cover plate, and with one of said grooves being located in the bottom of each of the said legs forming the U-shaped block.

11. An apparatus as defined in claim 10, and including a rigid bar extending across the top of the cover plate transversely to the parallel channels and releasably secured to the cover plate by a fastener;

and a second fastener securing the base part of the U-shaped block to the bar with the bottoms of the legs of the block, which contain the downwardly opening grooves covering the rows of filling and second holes, being clamped against the upper surface of the cover plate.

12. An apparatus as defined in claim 9, wherein said manifold block is formed of a transparent, plastic material, and having a lower surface arranged to engage the upper surface of the cover plate in face-to-face contact therewith, and said manifold grooves being formed in the manifold block lower surface, and with the peripheral edge portions of the grooves being releasably sealed against the cover plate upper surface.

13. An apparatus for use in blot screening solutions of antibody and the like materials by simultaneously, separately reacting a substantial number of microliter-size volume samples of such material with an antigen-like pattern carried upon a paper-like membrane, comprising:

a base plate having a flat support surface and a cover plate having a lower, flat, cover surface overlapping the base plate support surface;

manually operable screws extending through the cover plate into threaded openings in the base plate for manually releasably clamping the two plates together;

an array of a substantial number of parallel, closely spaced, elongated, shallow, very narrow, downwardly opening channels formed in the cover plate lower surface separated by stripe-like portions;

means defining holes extending through the cover plate for communicating each channel with the upper portion of the cover plate for conveying liquid specimens into and out of the channels;

a thin, resilient, spongy cushion sheet positioned upon the base plate support surface beneath the channels, and a membrane removably positioned upon the cushion sheet and in face-to-face contact with the cover plate lower surface covering each of the downwardly extending openings of the channels;

said membrane being adapted for screening samples of liquid materials;

said cushion sheet being of a relatively low density so that it is characterized by having sufficient resiliency to be compressed between the cover plate areas located between adjacent channels, while resiliently bulging towards the channel openings so as to bulge the membrane into the channels considerably reducing the interior volume of the channels while increasing the membrane surface area which is exposed to liquids contained within each channel;

wherein a sample of a liquid material may be introduced within at least one of the channels and another sample of a different material may be introduced within at least one of the other channels, with the membrane located at the channel openings bulged by the cushion sheet and exposed to the samples, whereby leakage between adjacent channels is substantially prevented.

14. An apparatus as defined in claim 13, wherein the holes into each channel are arranged in two rows, one row near one end of the channels and the other row near the opposite end of the channels; and further including a manifold block having a lower surface releasably engaged with the cover plate at an upper surface thereof and having downwardly opening grooves overlapping the two rows of holes, with each groove communicating through a passageway to the lower surface of the block so that liquid may be inserted through one groove into all of the channels simultaneously through one row of holes and removed from all of the channels through the opposite row of holes;

and further including releasable fastening means securing the manifold block in engagement to the upper surface of the cover plate so that the block may be applied upon or removed from the cover plate while the cover plate remains clamped to the base plate by the manually operable screws.

15. An apparatus as defined in claim 14, and including a resilient sealing ring arranged around each of said manifold block grooves and sealing against the adjacent cover plate portions around the respective rows of holes.

16. An apparatus as defined in claim 14, and said manifold block being formed of a transparent, plastic material so that the grooves and passageways may be visually observed during use thereof.

17. An apparatus as defined in claim 14, wherein said manifold block releasable fastening means comprises manually operable screws which extend through and fasten the block, the cover plate and base plate together, and which can be manually released, for removing the block, and replaced for fastening the base plate and cover plate together without the manifold block.

18. An apparatus as defined in claim 13, wherein said membrane includes a nitrocellulose material.

19. An apparatus as defined in claim 18, wherein said cushion sheet includes a polyethylene material.

* * * * *